(12) United States Patent
Tsuda

(10) Patent No.: US 9,996,172 B2
(45) Date of Patent: Jun. 12, 2018

(54) TARGET SETTING APPARATUS

(71) Applicant: DENSO CORPORATION, Kariya, Aichi-pref. (JP)

(72) Inventor: Yoshiyuki Tsuda, Kariya (JP)

(73) Assignee: DENSO CORPORATION, Kariya, Aichi-pref. (JP)

( * ) Notice: Subject to any disclaimer, the term of this patent is extended or adjusted under 35 U.S.C. 154(b) by 45 days.

(21) Appl. No.: 15/310,853

(22) PCT Filed: Apr. 7, 2015

(86) PCT No.: PCT/JP2015/001951
§ 371 (c)(1),
(2) Date: Nov. 14, 2016

(87) PCT Pub. No.: WO2015/190022
PCT Pub. Date: Dec. 17, 2015

(65) Prior Publication Data
US 2017/0108940 A1  Apr. 20, 2017

(30) Foreign Application Priority Data

Jun. 11, 2014  (JP) ................................ 2014-120679

(51) Int. Cl.
*G06K 9/00* (2006.01)
*G06F 3/038* (2013.01)
(Continued)

(52) U.S. Cl.
CPC .............. *G06F 3/038* (2013.01); *A61B 3/113* (2013.01); *B60K 35/00* (2013.01); *G06F 3/013* (2013.01);
(Continued)

(58) Field of Classification Search
CPC ................ G06K 9/00; G06T 7/00; G06F 3/00
(Continued)

(56) References Cited

U.S. PATENT DOCUMENTS 7,492,957 B1 * 2/2009 Bonhaus .............. G06K 9/6206
                                                  348/384.1
9,881,227 B2 * 1/2018 Miyashita ............ G06K 9/4604

FOREIGN PATENT DOCUMENTS

JP     2000010723 A    1/2000
JP     2012065781 A    4/2012

OTHER PUBLICATIONS

Laurnet Itti, Christof Koch, & Ernst Niebur, "A Model of Saliency-Based Visual Attention for Rapid Scene Analysis", IEEE Transactions on Pattern Analysis and Machine Intelligence, Dec. 1998, 20(11):1254-1259.

* cited by examiner

*Primary Examiner* — Abolfazl Tabatabai
(74) *Attorney, Agent, or Firm* — Harness, Dickey & Pierce, P.L.C.

(57) ABSTRACT

A target setting apparatus sets a target correcting a sight line detection portion to detect a sight line of a subject person. A deviation between a position of the target and a position detected as a center of the sight line detected by the sight line detection portion when the subject person is estimated to be gazing at the target is regarded as a detection error and applied to a correction. The target setting apparatus includes: a sight line range estimation portion that estimates a sight line range; a candidate point extraction portion that extracts a candidate point for the target from the sight line range; a candidate point evaluation portion that evaluates appropriateness of the candidate point as the target by using a plurality of indices; and a target setting portion that determines whether or not to set the candidate point as the target.

7 Claims, 3 Drawing Sheets

(51) Int. Cl.
    *A61B 3/113*         (2006.01)
    *G06T 7/80*          (2017.01)
    *B60K 35/00*        (2006.01)
    *G06F 3/01*          (2006.01)
    *G06K 9/03*          (2006.01)
    *G06F 3/0484*       (2013.01)
    *H04N 5/225*       (2006.01)

(52) U.S. Cl.
    CPC ....... *G06F 3/04842* (2013.01); *G06K 9/0061* (2013.01); *G06K 9/00604* (2013.01); *G06K 9/00845* (2013.01); *G06K 9/036* (2013.01); *G06T 7/80* (2017.01); *B60K 2350/1008* (2013.01); *G06T 2207/30201* (2013.01); *G06T 2207/30268* (2013.01)

(58) Field of Classification Search
    USPC ........ 382/103, 236; 348/169, 170, 171, 172, 348/352
    See application file for complete search history.

TARGET SETTING APPARATUS

CROSS REFERENCE TO RELATED APPLICATIONS

This application is a U.S. National Phase Application under 35 U.S.C. 371 of International Application No. PCT/JP2015/001951 filed on Apr. 7, 2015 and published in Japanese as WO 2015/190022 A1 on Dec. 17, 2015. This application is based on and claims the benefit of priority from Japanese Patent Application No. 2014-120679 filed on Jun. 11, 2014. The entire disclosures of all of the above applications are incorporated herein by reference.

TECHNICAL FIELD

The present disclosure relates to a target setting apparatus that sets a target for correcting a sight line detection portion that detects a sight line of a subject person.

BACKGROUND ART

Conventionally, there are various devices that include a sight line detection portion, which detects the sight line of a subject person, and exercise control on the basis of the detected sight line. A certain proposed device displays an array of cursors, which each show a character, on an input dialog screen of a personal computer. When a specific cursor is gazed at, the device determines that an instruction is issued to input the character associated with the cursor (referring to Patent Literature 1, for example).

Further, the configuration described in Patent Literature 1 sets a target at the center of each cursor and automatically corrects the sight line detection portion. More specifically, when the sight line detection portion estimates that a specific cursor is gazed at, the deviation between a position that is detected as the center of a sight line by the sight line detection portion and a central position (a target) of the specific cursor is regarded as a detection error of the sight line detection portion and applied to the correction. In the configuration described in Patent Literature 1, the sight line detection portion is formed by a sight line sensor detecting an eyeball rotation angle and a process performed on the eyeball rotation angle, and the deviation is reflected in correction data used during the process performed on the eyeball rotation angle. The detection error not only includes an error caused by the sight line detection portion, but also an error caused by eyeball movement peculiar to the subject person (this applies hereinafter).

The inventor of the present disclosure has found the following. The configuration described in Patent Literature 1 sets a target at the center of a cursor displayed on a predetermined portion of the input dialog screen. Therefore, when a screen has a pattern or array that is not initially imagined by a designer of the device, the target cannot be set in a proper manner. Further, the sight line detection portion may detect the sight line of the subject person even when the subject person is looking at the outside. In such an instance, too, it is preferred that the target be properly set.

PRIOR ART LITERATURE

Patent Literature

Patent Literature 1: JP 2000-10723 A

SUMMARY OF INVENTION

It is an object of the present disclosure to provide a target setting apparatus that is capable of properly setting a target for correcting the sight line detection portion irrespective of an image presented to the eyes of the subject person.

According to one aspect of the present disclosure, a target setting apparatus sets a target for correcting a sight line detection portion to detect a sight line of a subject person, a deviation between a position of the target and a position detected as a center of the sight line detected by the sight line detection portion when the subject person is estimated to be gazing at the target being regarded as a detection error of the sight line detection portion and being applied to a correction. The target setting apparatus includes: a sight line range estimation portion that estimates a sight line range within which the sight line of the subject person moves; a candidate point extraction portion that extracts a candidate point for the target from the sight line range, which is estimated by the sight line range estimation portion; a candidate point evaluation portion that evaluates appropriateness of the candidate point as the target by using a plurality of indices, the candidate point being extracted by the candidate point extraction portion; and a target setting portion that determines, based on the appropriateness evaluated by the candidate point evaluation portion as the target, whether or not to set the candidate point as the target.

The target setting apparatus according to the present disclosure extracts candidate points for a target and evaluates the extracted candidate points by using multiple indices. Therefore, it is possible to evaluate the candidate points extracted from the sight line range within which the sight line of the subject person moves by using the multiple of indices irrespective of an image presented to the eyes of the subject person. Thus, it is possible to properly set the target for correcting the sight line detection portion irrespective of an image presented to the eyes of the subject person.

BRIEF DESCRIPTION OF DRAWINGS

The above and other aspects, features and advantages of the present disclosure will become more apparent from the following detailed description made with reference to the accompanying drawings. In the drawings.

PREFERRED EMBODIMENTS FOR CARRYING OUT INVENTION

Configuration of Present Embodiment

Figure 1:
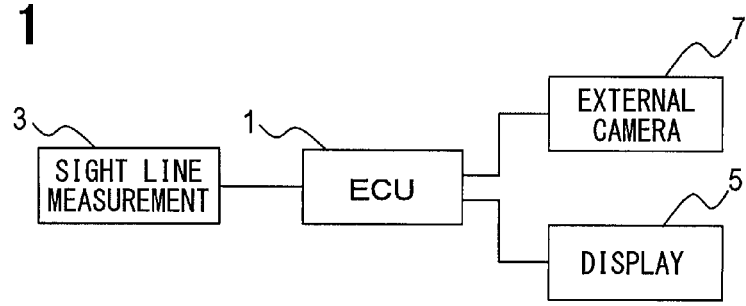
FIG. 1 is a block diagram illustrating a configuration of an onboard apparatus.

An embodiment of the present disclosure will be described with reference to the drawings. An onboard apparatus (a vehicle onboard apparatus) illustrated in FIG. 1 is mainly configured from an ECU 1. The ECU 1 is connected to a sight line measurement portion 3, a display 5, and an external camera 7. The sight line measurement portion 3 is a known device that detects the sight line (an eye gaze) of a driver of a vehicle. The display 5 is a known device that is also used, for example, as a display screen of a car navigation device. The external camera 7 is a known device used, for instance, with an event data recorder in order to capture an image forward of the vehicle.

Process Performed According to Embodiment

Figure 2:
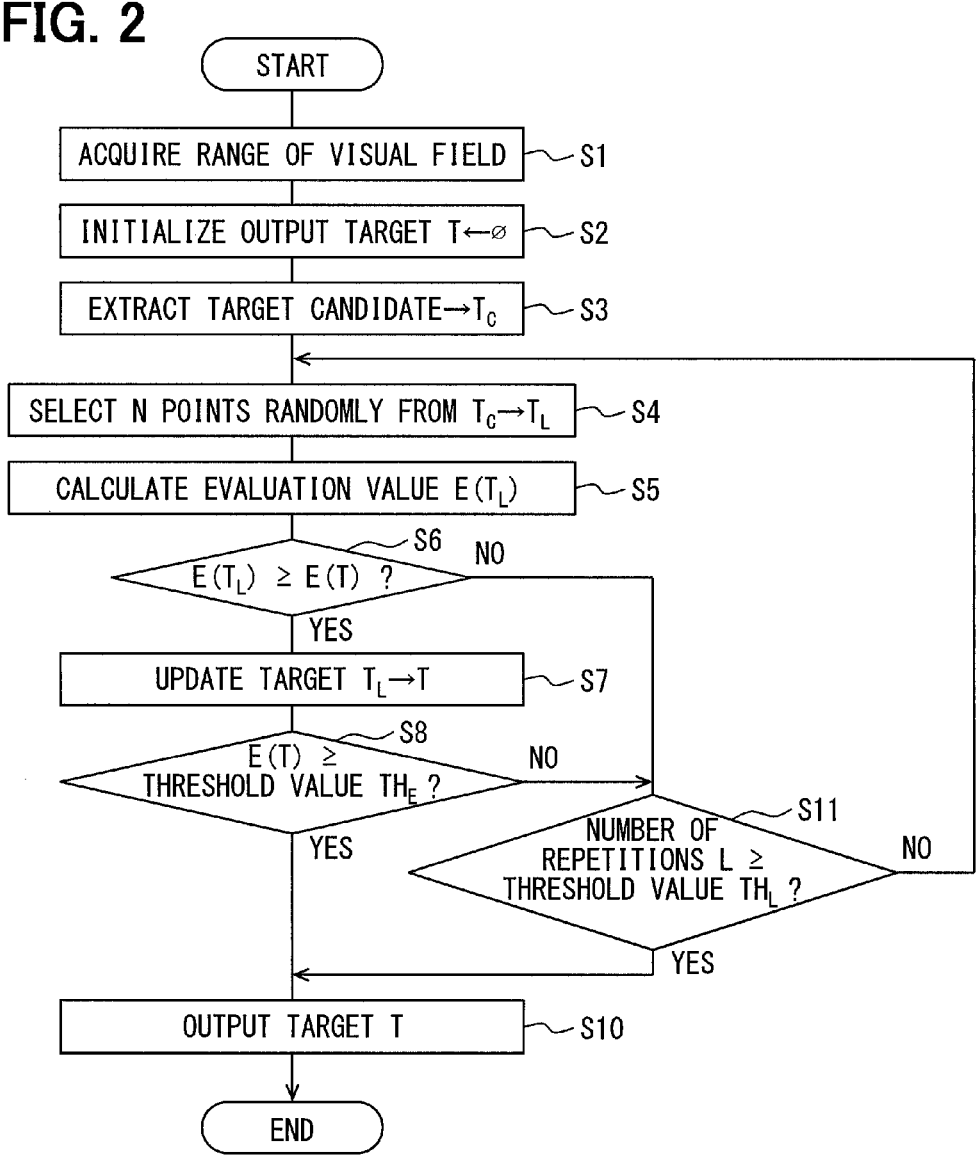
FIG. 2 is a flowchart illustrating a part of a process performed by the onboard apparatus.

FIG. 2 is a flowchart illustrating a process that is performed by a CPU built in the ECU 1 in compliance with a program stored in a ROM built in the ECU 1. The process is performed repeatedly on a periodic basis while the sight line measurement portion 3 operates. The process is performed to set a target in order to correct (perform a calibration of) the sight line measurement portion 3. More specifically, when the target is set, the deviation between the position of the target and a position that is detected as the center of the sight line of the driver by the sight line measurement portion 3 when the driver is supposed to be gazing at the target is regarded as a detection error of the sight line measurement portion 3 and applied to the correction.

As illustrated in FIG. 2, the range of a visual field of the driver is initially acquired in S1 ("S" is an abbreviation of "step"; this applies hereinafter) of the process. Here, the visual field denotes a range narrower than a medical visual field and, more specifically, denotes a sight line range within which the sight line (the center of the sight line) of a subject person (a driver) moves. The range of the visual field may be acquired in various manners. For example, when the driver is supposed to be looking at the display 5, the screen S (see FIG. 3) of the display 5 may be acquired as the range of the visual field. Meanwhile, when the driver is supposed to be driving the vehicle, the image capture range of the external camera 7 may be acquired as the range of the visual field.

Next, in S2, the target that has been outputted (set) thus far is initialized. In S3, multiple (>>N>>1) of target candidate points are extracted from the range of the visual field acquired in S1, and a group of such points is assumed to be $T_C$. In S4, N points are randomly selected from $T_C$, which has extracted in S3, and a group of such points (candidate points) are assumed to be a candidate point group $T_L$ (a candidate point set). In S5, an evaluation value E ($T_L$) of the candidate point group $T_L$ is calculated, for instance, from Equation (1) below.

$$E(T_L) = E_S(T_L) + E_A(T_L) + E_C(T_L) \qquad (1)$$

Figure 3:
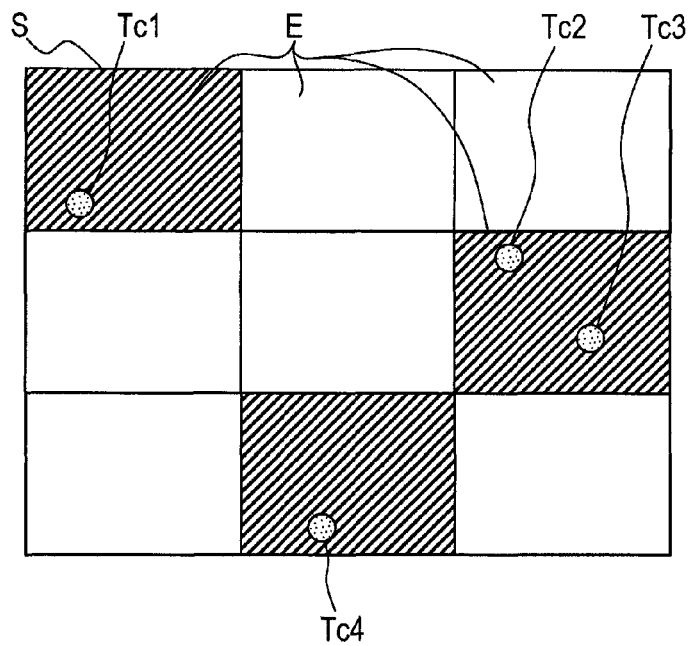
FIG. 3 is a diagram illustrating an example of an evaluation value of target candidates.

In Equation (1), the evaluation value $E_S$ ($T_L$) is an index indicative of the degree of dispersion of candidate points relative to the whole range of the visual field, and is calculated, for example, in a manner described below. In the example of FIG. 3, the candidate points Tc1-Tc4 exist in some of areas E, which are obtained when the screen S of the display 5 is equally divided into nine (3×3) segments. The number of areas E where the candidate points Tc1-Tc4 exist, that is, a screen coverage percentage of the candidate points Tc1-Tc4, is calculated and assumed to be the evaluation value $E_S$ ($T_L$). The evaluation value $E_S$ ($T_L$) calculated in the above manner may be normalized by dividing it by the number of candidate points Tc1-Tc4.

Figure 4:
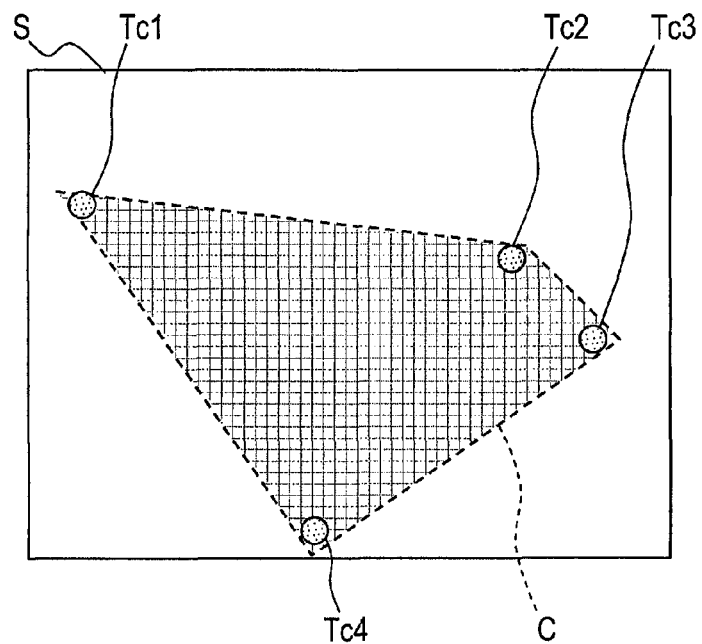
FIG. 4 is a diagram illustrating another example of the evaluation value of target candidates.

FIG. 4 is a diagram illustrating another method of calculating the evaluation value $E_S$ ($T_L$). In the example of FIG. 4, a convex hull C is assumed as a convex polygon including all the candidate points Tc1-Tc4, and the area of the convex hull C is calculated and regarded as the evaluation value Es ($T_L$). Incidentally, the evaluation value Es ($T_L$) in Equation (1) may be calculated by a method other than described above. Further, values calculated by the various methods may be combined and used as the evaluation value.

In Equation (1), an evaluation value $E_A$ ($T_L$) is an index indicative of noticeability of candidate points and calculated, for example, as described below. A conspicuousness map can be created on the basis of visual features, and a value obtaining by adding up the conspicuousness (saliency) of each candidate point can be used as the evaluation value $E_A$ ($T_L$). The calculation of such conspicuousness will not be described in detail here since it is described in detail, for example, in Itti, L., Koch, C., & Niebur, E., 1998, A Model of Saliency-Based Visual Attention for Rapid Scene Analysis, IEEE Transactions on Pattern Analysis and Machine Intelligence. According to this literature, an optic nerve greatly responds to a region significantly different from the surroundings, for example, in brightness, hue, and orientation, that is, such a region is highly conspicuous. Further, the conspicuousness of each candidate point may be calculated including dynamic elements such as blinking light or calculated based on only the dynamic elements.

Figure 5:
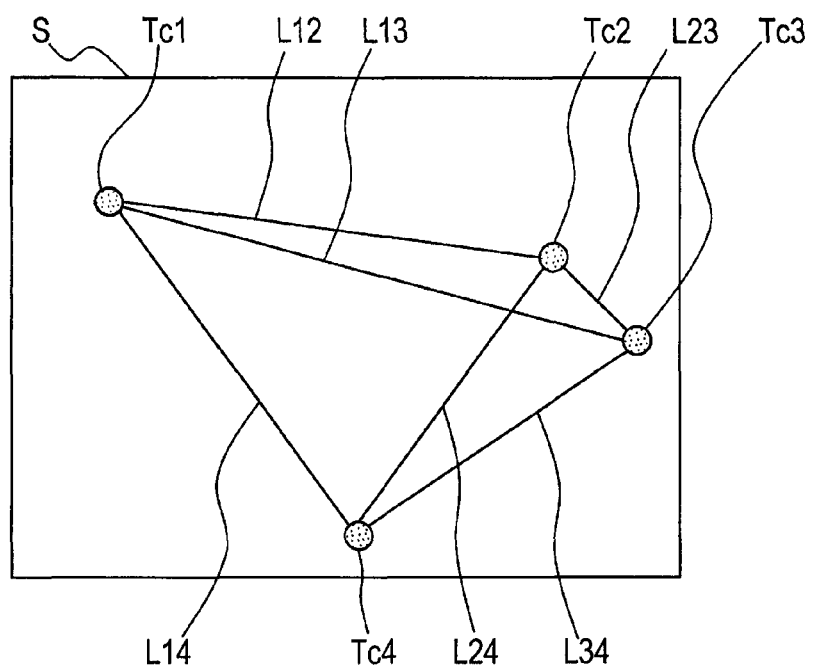
FIG. 5 is a diagram illustrating still another example of the evaluation value of target candidates.

In Equation (1), an evaluation value $E_C$ ($T_L$) is an index indicative of non-confusability of candidate points and calculated, for example, as described below. The longer the distance between two candidate points (two of candidate points Tc1-Tc4), the more non-confusable the two candidate points will be. Thus, as illustrated in FIG. 5, a line segment connecting a candidate point Tcm to a candidate point Tcn may be assumed to be Lmn (m, n=1, 2, 3, or 4), and the total length of line segments L12-L34 may be regarded as the evaluation value $E_C$ ($T_L$). Further, when three candidate points are arranged on a straight line, they are also confusable. Thus, the areas of triangles formed by three arbitrarily selected candidate points Tc1-Tc4 may be calculated, and the sum of the areas may be regarded as the evaluation value $E_C$ ($T_L$). Furthermore, the evaluation value $E_C$ ($T_L$) calculated by the above methods may be normalized by dividing it by the number of line segments or by the number of candidate points. The evaluation value $E_C$ ($T_L$) may be calculated by a method other than described above.

Returning to FIG. 2, after the evaluation value E ($T_L$) for the candidate point group $T_L$ is calculated in S5 as described above, it is determined in S6 whether the calculated evaluation value E ($T_L$) is equal to or more than the maximum value E (T) of evaluation values E ($T_L$) for the other candidate point sets $T_L$. When E ($T_L$)≥E (T) (S6: YES), the processing shifts to S7. When S6 is initially performed after the start of the process described in FIG. 2, the value E (T) is reset to 0 (zero). Therefore, it is determined that E ($T_L$)≥E (T) (S6: YES) without regard to the candidate point group $T_L$ selected in S4, and the processing proceeds to S7.

In S7, the candidate point group $T_L$ is temporarily set (updated) as a target group T (a target set T) formed of N target points. Next, in S8, it is determined whether the evaluation value E (T) for the target group T, that is, the evaluation value E ($T_L$), is equal to or more than a threshold value $TH_E$. If E (T)≥$TH_E$ (S8: YES), the processing proceeds to S10. In S10, the target group T is outputted as a correction target for the sight line measurement portion 3. Upon completion of S10, processing terminates for a time.

Subsequently, when the driver is supposed to be gazing at a certain point (a target) included in the target group T, the detection error of the sight line measurement portion 3 is corrected based on the deviation between the position of the target and a position detected as the center of the sight line of the driver by the sight line measurement portion 3. This calibration process is performed as a process separate from the one illustrated in FIG. 2 while the driver is unconsciously looking at the display 5. This kind of calibration process will not be described in detail here since it is well known.

When the evaluation value $E(T_L)$ is smaller than the threshold value $TH_E$ (S8: NO) or the evaluation value $E(T_L)$ for the candidate point group $T_L$ is smaller than the previously calculated evaluation values $E(T)$ (S6: NO), processing proceeds to S11. In S11, it is determined whether the number L of repetitions of S4 to S5 is equal to or more than a threshold value $TH_L$. When the number L of repetitions is smaller than the threshold value $TH_L$ (S11: NO), processing returns to S4. When the number L of repetitions is greater than or equal to the threshold value $TH_L$ (S11: YES), processing proceeds to S10. More specifically, when no candidate point group $T_L$ having an evaluation value $E(T_L)$ equal to or more than the threshold value $TH_E$ is encountered even when the candidate point group $T_L$ is reselected (S4) $TH_L$ times (S8: NO, S11: YES), a candidate point group $T_L$ having the greatest evaluation value $E(T_L)$ is set as the target group T (S10).

Effects and Modifications of Embodiment

As described above, the present embodiment evaluates the appropriateness of a candidate point group $T_L$ as the target group T by selecting the candidate point group $T_L$ and calculating the evaluation value $E(T_L)$ through the use of multiple indices. Therefore, it is possible to properly evaluate the candidate point group $T_L$ irrespective of an image presented to the eyes of the driver. For example, even if an image displayed on the display 5 is edited in a manner unpredicted by a program producer, for instance, by inserting an animation into a part of the displayed image, the ECU 1 acquires information about the edited image. It is possible for the ECU 1 to properly calculate the evaluation value $E(T_L)$ for a selected candidate point group $T_L$.

The examples of FIGS. 3 to 5 illustrate a case where an image displayed on the screen S of the display 5 is set as the target. Alternatively, an image captured by the external camera 7 may be set as the target. When such an alternative scheme is employed, the image capture range of the external camera 7 is regarded as the range of a visual field and set as the target as mentioned earlier. In such an instance, a candidate point that is set on an on-street blue signboard (a signpost or a guide sign) may be determined to be readily noticeable (provided with a great evaluation value $E_A(T_L)$). When the image captured by the external camera 7 is set as the target, readily-noticeable candidate points include not only signposts but also speed limit and other signs, traffic lights (particularly a change in color), brake lamps of a preceding vehicle, pedestrians, bicycles, on-road obstacles, and convex traffic mirrors.

In the embodiment, the ECU 1 corresponds to an example of a sight line range estimation portion, an example of a candidate point extraction portion, an example of a candidate point evaluation portion, an example of a target setting portion, and an example of a target setting apparatus including the four portions. Further, the sight line measurement portion 3 corresponds to an example of a sight line detection portion (also be referred to as a sight line detector), the display 5 corresponds to an example of a display portion, and the external camera 7 corresponds to an example of an image capture portion. Furthermore, S1 of processing performed by the ECU 1 corresponds to an example of the sight line range estimation portion, S3 and S4 correspond to an example of the candidate point extraction portion, S5 corresponds to an example of the candidate point evaluation portion, and S6 to S11 correspond to an example of the target setting portion.

The target setting apparatus is not limited to the present embodiment, and may be implemented in various ways without departing from the spirit of the present disclosure. For example, the evaluation value $E(T_L)$ to be calculated from Equation (1) may be calculated without using one of the evaluation values $E_S(T_L)$, $E_A(T_L)$, $E_C(T_L)$ associated with the indices.

However, when one of the indices indicates the degree of dispersion of candidate points, which form a candidate point group, relative to the whole range of the visual field, as is the case with the evaluation value $E_S(T_L)$, the following effect will be produced. When multiple targets are set in a uniformly dispersed manner within the whole range of the visual field, the detection error can be determined for each of the uniformly dispersed targets even when the detection error of the sight line measurement portion 3 varies from one segment to another within the range of the visual field. Therefore, when each candidate point configuring a candidate point group is set as a target when the candidate point group is evaluated to be high in the degree of dispersion within the whole range of the visual field, it is possible to properly correct the sight line measurement portion 3 extensively within the range of the visual field.

Further, when one of the indices indicates non-confusability of candidate points, as is the case with the evaluation value $E_C(T_L)$, the following effect is produced. Even in a situation where multiple targets are set, it is not always possible to accurately estimate which target the driver is gazing at when readily-confusable targets exist (the degree of non-confusability is low) since, for instance, the targets are positioned close to each other or arranged on a straight line. When, by contrast, the degree of non-confusability of the candidate points is high, which target the driver is gazing at can be estimated more accurately. Thus, it is possible to correct the sight line measurement portion 3 more properly.

Furthermore, when one of the indices indicates noticeability of candidate points, as is the case with the evaluation value $E_A(T_L)$, the following effect is produced. In reality, a readily-noticeable point within the range of the visual field is frequently gazed at by the driver. When such a point is set as the target, the process of correcting the sight line measurement portion 3 after estimating that the driver is gazing at the target may be performed more frequently. Additionally, the target is actually gazed at for a long period of time. Therefore, when a candidate point evaluated to be high in noticeability is set as the target, it is possible to correct the sight line measurement portion 3 more accurately.

When only multiple indices capable of calculating the evaluation value for a single candidate point are used as in the case of noticeability, one target point may be set based on the result of evaluation of each extracted candidate point. The target setting apparatus is not limited to an onboard apparatus and may be applied to a personal computer and various other apparatus.

When the candidate point extraction portion extracts a candidate point group including multiple candidate points, one of the multiple indices may indicate the degree of dispersion within the whole sight line range of each candidate point included in the candidate point group. When multiple targets are set in a uniformly dispersed manner within the whole sight line range, it is possible to determine the detection error for each of the uniformly dispersed targets, even when the detection error of the sight line detection portion varies from one segment to another within the sight line range. Therefore, individual candidate points forming a candidate point group evaluated to be high in the degree of dispersion within the whole range of the visual field are set as targets, it is possible to correct the sight line detection portion properly and extensively within the sight line range.

When the candidate point extraction portion extracts a candidate point group formed of multiple candidate points, one of the multiple indices may indicate the non-confusability of the candidate points forming the candidate point group. Even when multiple targets are set, it is not always possible to accurately estimate which target a subject person is gazing at when readily-confusable targets exist (the degree of non-confusability is low) since, for instance, the targets are positioned close to each other or arranged on a straight line. When the degree of non-confusability of the candidate points is high, it is possible to estimate which target the driver is gazing at more accurately. Thus, it is possible to correct the sight line measurement portion more properly.

Further, one of the multiple indices may indicate the noticeability of the candidate points. In reality, a readily-noticeable point within the sight line range is frequently gazed at by the subject person. When such a point is set as the target, the process of correcting the sight line detection portion after estimating that the subject person is gazing at the target can be performed more frequently. Additionally, the target is actually gazed at for a long period of time. Therefore, when a candidate point evaluated to be high in noticeability is set as the target, the sight line detection portion can be corrected more accurately.

It is noted that a flowchart or the processing of the flowchart in the present application includes multiple steps (also referred to as sections), each of which is represented, for instance, as S1. Further, each step can be divided into several sub-steps while several steps can be combined into a single step.

While various embodiments, configurations, and aspects of the target setting apparatus have been exemplified, the embodiments, configurations, and aspects of the present disclosure are not limited to those described above. For example, embodiments, configurations, and aspects obtained from an appropriate combination of technical elements disclosed in different embodiments, configurations, and aspects are also included within the scope of the embodiments, configurations, and aspects according to the present disclosure.

What is claimed is:

1. A target setting apparatus that sets a target correcting a sight line detection portion to detect a sight line of a subject person, a deviation between a position of the target and a position detected as a center of the sight line detected by the sight line detection portion when the subject person is estimated to be gazing at the target being regarded as a detection error of the sight line detection portion and being applied to a correction, the target setting apparatus comprising:
    a sight line range estimation portion that estimates a sight line range within which the sight line of the subject person moves;
    a candidate point extraction portion that extracts a candidate point (Tc) for the target from the sight line range, which is estimated by the sight line range estimation portion;
    a candidate point evaluation portion that evaluates appropriateness of the candidate point as the target by using a plurality of indices, the candidate point being extracted by the candidate point extraction portion; and
    a target setting portion that determines, based on the appropriateness evaluated by the candidate point evaluation portion as the target, whether or not to set the candidate point as the target.

2. The target setting apparatus according to claim 1, wherein:
    the candidate point extraction portion extracts a candidate point group including a plurality of candidate points;
    the candidate point evaluation portion evaluates appropriateness of the candidate point group as a target group including a plurality of targets, the candidate point group being extracted by the candidate point extraction portion; and
    the target setting portion determines, based on the appropriateness as the target group, whether or not to set each of the candidate points providing the candidate point group as the target, the target group being evaluated by the candidate point evaluation portion.

3. The target setting apparatus according to claim 2, wherein:
    one of the plurality of indices indicates a degree of dispersion of the candidate points providing the candidate point group relative to a whole of the sight line range.

4. The target setting apparatus according to claim 2, wherein:
    one of the plurality of indices indicates a degree of non-confusability of the candidate points providing the candidate point group.

5. The target setting apparatus according to claim 1, wherein:
    one of the plurality of indices indicates a degree of noticeability of candidate points.

6. The target setting apparatus according to claim 1, wherein:
    the sight line range estimation portion estimates a screen of a display portion presenting an image to the subject person as the sight line range;
    the candidate point extraction portion extracts a point on the screen as the candidate point; and
    the candidate point evaluation portion evaluates the appropriateness based on information about an image displayed on the screen.

7. The target setting apparatus according to claim 1, wherein:
    the subject person includes a driver of a vehicle;
    the sight line range estimation portion estimates an image capture range of an image capture portion as the sight line range, the image capture portion capturing an image forward of the vehicle;
    the candidate point extraction portion extracts a point on the image captured by the image capture portion as the candidate point; and
    the candidate point evaluation portion evaluates the appropriateness based on the image captured by the image capture portion.

* * * * *